(12) United States Patent
Funderburk

(10) Patent No.: US 10,918,873 B2
(45) Date of Patent: Feb. 16, 2021

(54) SYSTEMS AND METHODS FOR MAKING AND USING AN ENHANCED CONNECTOR OF AN ELECTRICAL STIMULATION SYSTEM

(71) Applicant: Boston Scientific Neuromodulation Corporation, Valencia, CA (US)

(72) Inventor: Jeffery Van Funderburk, Stevenson Ranch, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 265 days.

(21) Appl. No.: 16/041,355

(22) Filed: Jul. 20, 2018

(65) Prior Publication Data

US 2019/0030345 A1  Jan. 31, 2019

Related U.S. Application Data

(60) Provisional application No. 62/536,839, filed on Jul. 25, 2017.

(51) Int. Cl.
*A61N 1/375* (2006.01)
*A61N 1/05* (2006.01)
(Continued)

(52) U.S. Cl.
CPC ......... *A61N 1/3754* (2013.01); *A61N 1/0551* (2013.01); *A61N 1/3752* (2013.01);
(Continued)

(58) Field of Classification Search
USPC .......................................................... 607/38
See application file for complete search history.

(56) References Cited

U.S. PATENT DOCUMENTS 3,222,471 A  12/1965  Steinkamp
3,601,747 A   8/1971  Prall et al.
(Continued)

FOREIGN PATENT DOCUMENTS

EP  0580928 A1  2/1994
EP  0650694 B1  7/1998
(Continued)

OTHER PUBLICATIONS

International Search Report and Written Opinion for PCT Application No. PCT/US2018/043119 dated Nov. 12, 2018.

*Primary Examiner* — Kennedy Schaetzle
(74) *Attorney, Agent, or Firm* — Branch Partners PLLC; Bruce E. Black

(57) ABSTRACT

An implantable control module for an electrical stimulation system includes a housing and a connector shell extending into the housing. The housing and the connector shell collectively form a sealed cavity. The connector shell has a longitudinal length, a sidewall with a cavity-facing surface, a first end open to an environment external to the housing, and an opposing closed second end. The connector shell defines a connector lumen extending within the connector shell and open at the first end to receive a portion of a lead or lead extension. Connector contacts are arranged along the connector lumen within the connector shell. An electronic subassembly is disposed in the sealed cavity. Interconnect conductors electrically couple the electronic subassembly to the connector contacts and extend from the connector shell within the sealed cavity.

20 Claims, 12 Drawing Sheets

(51) Int. Cl.
*A61N 1/372* (2006.01)
*A61N 1/04* (2006.01)
*A61N 1/36* (2006.01)
*A61N 1/08* (2006.01)

(52) U.S. Cl.
CPC .............. *A61N 1/0476* (2013.01); *A61N 1/05* (2013.01); *A61N 1/08* (2013.01); *A61N 1/36* (2013.01); *A61N 1/36062* (2017.08); *A61N 1/36071* (2013.01); *A61N 1/37211* (2013.01); *A61N 1/37223* (2013.01)

(56) References Cited

U.S. PATENT DOCUMENTS

| | | |
|---|---|---|
| 3,718,142 A | 2/1973 | Mulier |
| 3,757,789 A | 9/1973 | Shenker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shenker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,934,366 A * | 6/1990 | Truex .................. A61N 1/3752 607/37 |
| 4,951,687 A | 8/1990 | Ufford et al. |
| 4,995,389 A | 2/1991 | Harris |
| 5,000,177 A | 3/1991 | Hoffmann et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,029,089 A * | 2/2000 | Hawkins .............. A61N 1/3752 439/271 |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gard |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |

(56) References Cited

U.S. PATENT DOCUMENTS

| | | |
|---|---|---|
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B1 | 1/2004 | Ketterl et al. |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooj et al. |
| 7,027,852 B2 | 4/2006 | Helland |
| 7,047,084 B2 | 5/2006 | Erickson et al. |
| 7,058,452 B2 | 6/2006 | Dahlberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,819 B1 * | 9/2006 | O'Hara ............. A61N 1/3752 607/36 |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 * | 7/2007 | Brase ............. A61N 1/0551 439/668 |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 4/2009 | Marvin et al. |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,650,191 B1 | 1/2010 | Lim et al. |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,604,068 B2 | 3/2017 | Malinowski |

(56) References Cited

U.S. PATENT DOCUMENTS

| | | |
|---|---|---|
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 2001/0023368 A1 | 9/2001 | Black et al. |
| 2002/0128692 A1* | 9/2002 | Imani .................... A61N 1/3752 607/37 |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0050672 A1* | 3/2003 | Dahlberg ............. A61N 1/3752 607/37 |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2007/0255332 A1 | 11/2007 | Cabelka et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0198530 A1* | 8/2008 | Zhao .................... A61N 1/3754 361/307 |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0054949 A1* | 2/2009 | Alexander ............... A61N 1/05 607/37 |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffitt et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0296745 A1 | 10/2016 | Govea et al. |
| 2016/0375238 A1 | 12/2016 | Leven et al. |
| 2017/0072187 A1 | 3/2017 | Howard et al. |
| 2017/0143978 A1 | 5/2017 | Barker |
| 2017/0203104 A1 | 7/2017 | Nageri et al. |

(56) References Cited

U.S. PATENT DOCUMENTS

| | | |
|---|---|---|
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

* cited by examiner

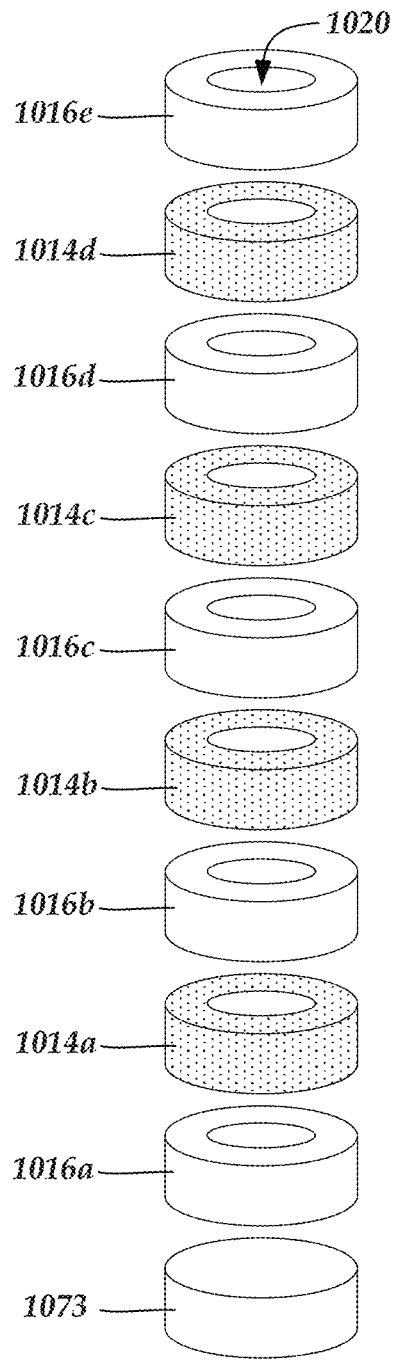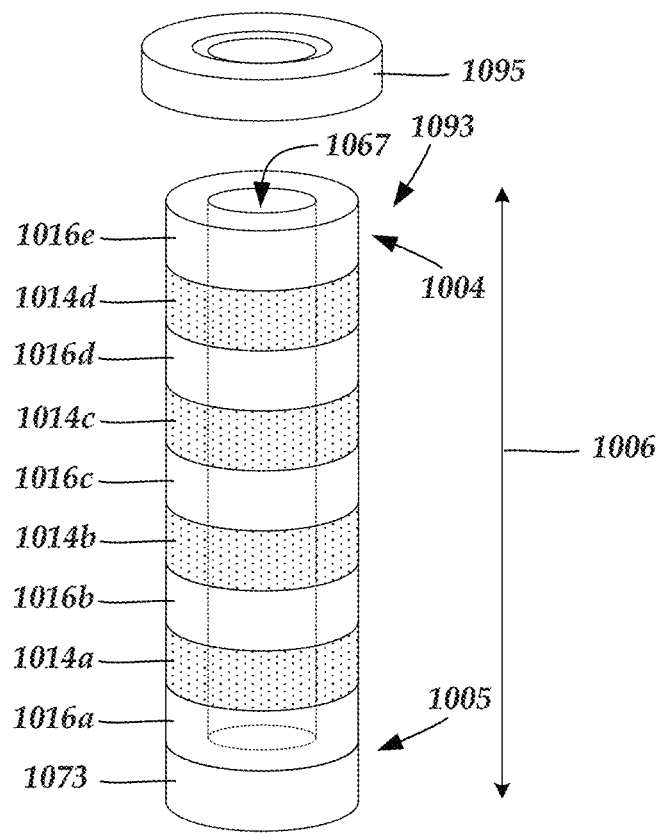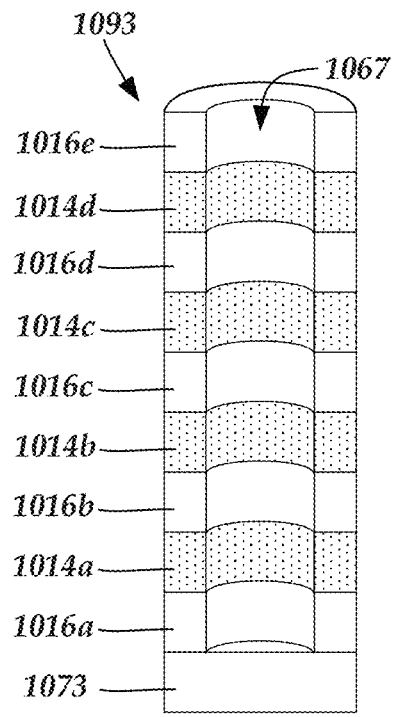
Fig. 10A
Fig. 10B
Fig. 10C

SYSTEMS AND METHODS FOR MAKING AND USING AN ENHANCED CONNECTOR OF AN ELECTRICAL STIMULATION SYSTEM

CROSS-REFERENCE TO RELATED APPLICATIONS

This application claims the benefit under 35 U.S.C. § 119(e) of U.S. Provisional Patent Application Ser. No. 62/536,839, filed Jul. 25, 2017, which is incorporated herein by reference.

FIELD

The present invention is directed to the area of implantable electrical stimulation systems and methods of making and using the systems. The present invention is also directed to systems and methods for providing a connector that extends into a housing of a control module of an electrical stimulation system and becomes part of a sealed cavity therewith, as well as methods of making and using the connector, control modules, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an implantable control module for an electrical stimulation system. The control module includes a housing and a connector shell extending into the housing. The housing and the connector shell collectively form a sealed cavity. The connector shell has a longitudinal length, a sidewall with a cavity-facing surface, a first end open to an environment external to the housing, and an opposing closed second end. The connector shell defines a connector lumen extending within the connector shell and open at the first end to receive a portion of a lead or lead extension. Connector contacts are arranged along the connector lumen within the connector shell. An electronic subassembly is disposed in the sealed cavity. Interconnect conductors electrically couple the electronic subassembly to the connector contacts and extend from the connector shell within the sealed cavity.

In at least some embodiments, the cavity is hermetically sealed. In at least some embodiments, the interconnect conductors extend entirely within the sealed cavity. In at least some embodiments, the connector shell is formed from at least one of ceramic or glass.

In at least some embodiments, the connector shell is formed from electrically conductive sections alternating along the longitudinal length of the connector shell with electrically nonconductive sections, where the electrically conductive sections and the electrically nonconductive sections are fixedly attached together. In at least some embodiments, the connector contacts include a first connector contact; the electrically conductive sections include a first electrically conductive section; and the first connector contact is electrically coupled to the first electrically conductive section. In at least some embodiments, the interconnect conductors include a first interconnect conductor electrically coupled to the first connector contact, the first interconnect conductor attached to the first electrically conductive section along the cavity-facing surface of the connector shell.

In at least some embodiments, electrically conductive vias are formed through the sidewall of the connector shell and electrically coupled to the connector contacts. In at least some embodiments, each of the electrically conductive vias is aligned along the longitudinal length of the connector shell, and electrically coupled, with a different one of the connector contacts. In at least some embodiments, the electrically conductive vias are brazed to the sidewall of the connector shell. In at least some embodiments, the electrically conductive vias are welded to the sidewall of the connector shell. In at least some embodiments, at least one of the interconnect conductors extends through at least one of the electrically conductive vias and attaches directly to one of the connector contacts. In at least some embodiments, at least one of the interconnect conductors electrically couples to at least one of the electrically conductive vias.

In another embodiment, an electrical stimulation system includes the control module described above; an electrical stimulation lead coupleable to the control module; and, optionally, a lead extension coupleable between the electrical stimulation lead and the control module.

In yet another embodiment, a method for making a control module includes inserting a connector contact into a connector lumen extending into an open first end of a connector shell, the connector lumen configured to receive a lead or lead extension; electrically coupling a first end of an interconnect conductor to the connector contact; electrically coupling an opposing second end of the interconnect conductor to an electronic subassembly; extending the connector shell into the housing with the first end of the connector shell open to an environment external to the housing; and creating a sealed cavity formed collectively by the connector shell and the housing, where the electronic subassembly is disposed in the sealed cavity, and where the interconnect conductor extends from the connector shell to the electronic subassembly within the sealed cavity.

In at least some embodiments, electrically coupling a first end of an interconnect conductor to the connector contact includes forming an electrically conductive via along an interconnect aperture defined along a sidewall of the connector shell. In at least some embodiments, forming an electrically conductive via along an interconnect aperture defined along a sidewall of the connector shell includes forming the electrically conductive via around the interconnect conductor electrically coupled to the connector contact. In at least some embodiments, electrically coupling a first end of an interconnect conductor to the connector contact includes electrically coupling the electrically conductive via to the connector contact and electrically coupling the first end of the interconnect conductor to the electrically conductive via.

In at least some embodiments, inserting a connector contact into a connector lumen extending into an open first end of a connector shell includes inserting a connector contact into a connector shell having an electrically conductive section electrically coupled to the connector contact and attached on both sides along a longitudinal length of the connector shell to a different electrically nonconductive section. In at least some embodiments, electrically coupling a first end of an interconnect conductor to the connector contact includes electrically coupling the first end of the interconnect conductor to a cavity-facing surface of the electrically conductive section of the connector shell.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 10A is a schematic perspective, exploded view of one embodiment of a stack of alternating rings of electrically conductive material and electrically nonconductive material, according to the invention;

FIG. 10B is a schematic perspective view of one embodiment of the alternating rings of FIG. 10A coupled together to form a connector shell with an elongated shape that is open on one end and defines a lumen suitable for receiving an elongated member, according to the invention;

FIG. 10C is a perspective longitudinal cross-sectional view of one embodiment of the connector shell of FIG. 10B, according to the invention;

DETAILED DESCRIPTION

The present invention is directed to the area of implantable electrical stimulation systems and methods of making and using the systems. The present invention is also directed to systems and methods for providing a connector that extends into a housing of a control module of an electrical stimulation system and becomes part of a sealed cavity therewith, as well as methods of making and using the connector, control modules, and electrical stimulation systems.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
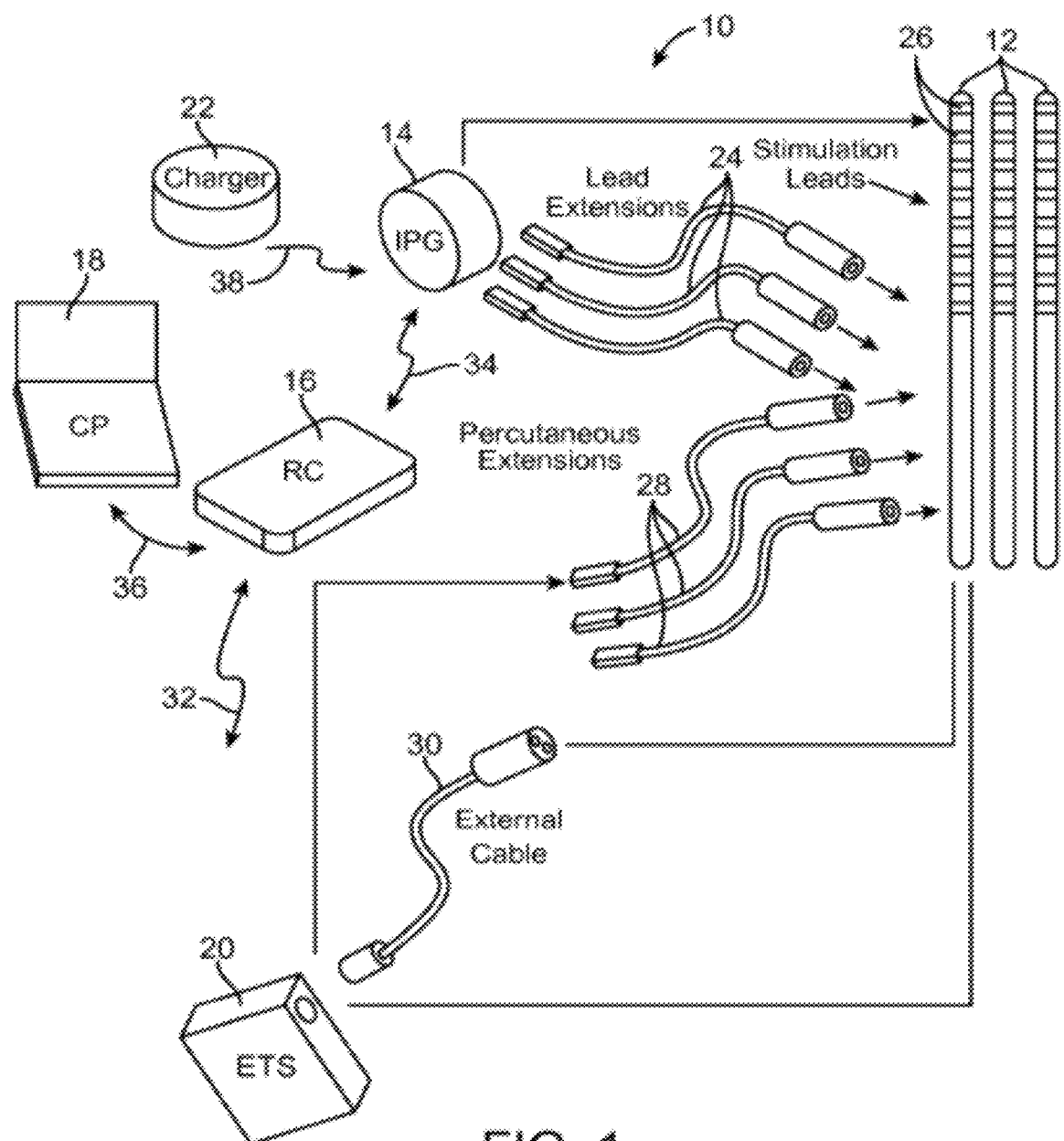
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally, via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
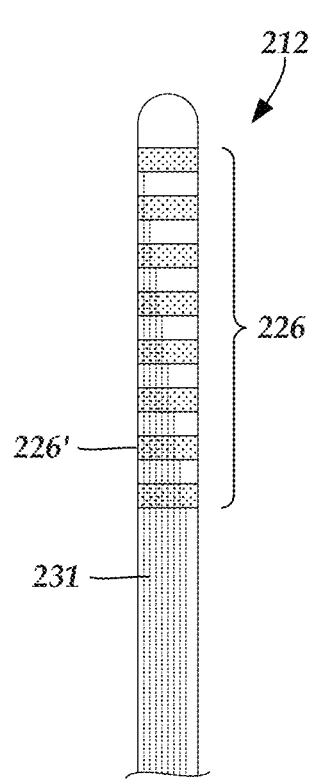
FIG. 2 is a schematic side view of one embodiment of an electrical stimulation lead, according to the invention.
Figure 2:
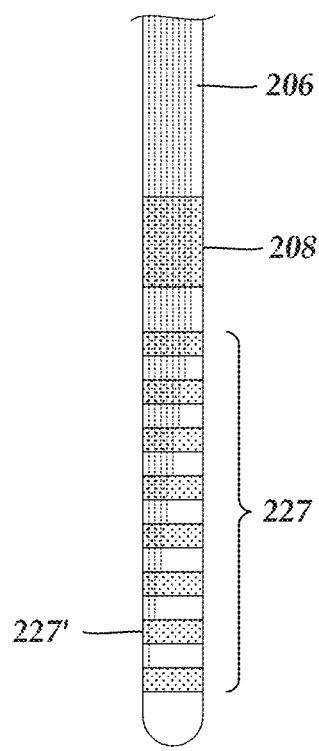

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. The leads described herein include 8 electrodes (+1 auxiliary electrode in some embodiments). It will be understood that the leads could include any suitable number of electrodes. The leads described herein exclusively include ring electrodes. It will be understood that the leads can include a distal-tip electrode, or one or more segmented electrodes in lieu of, or in addition to one or more ring electrodes. Additionally, the term "elongated member" used herein includes leads (e.g., percutaneous, paddle, cuff, or the like), as well as intermediary devices (e.g., lead extensions, adaptors, splitters, or the like).

FIG. 2 shows, in schematic side view, one embodiment of a lead 212 suitable for implanting into a patient and providing electrical stimulation. In some embodiments, the lead 212 is coupled directly to a control module. In other embodiments, the lead 212 is coupled to the control module via one or more intermediary devices. In the illustrated embodiment, an array of electrodes 226, which includes electrode 226', is disposed along a distal portion of a lead body 206 lead and an array of lead terminals 227, which includes lead terminal 227', is disposed along a proximal portion of the lead body. Lead conductors, such as lead conductor 231, extend along a longitudinal length of the lead and electrically couple the array of electrodes 226 to the array lead terminals 227.

Conductors can extend along the longitudinal length of the lead within one or more lumens defined in the lead. In other instances, the conductors may extend along the lead within the lead body itself. The lead 212 includes an auxiliary terminal 208 disposed along the proximal portion of the body to facilitate coupling of the proximal portion of the lead to a connector. The connector may be disposed along a control module. Alternatively, the auxiliary terminal 208 can be used to facilitate coupling of the proximal portion of the lead to a connector of an intermediary device, such as a lead extension which, in turn, is coupled to a connector of a control module.

Figure 3:
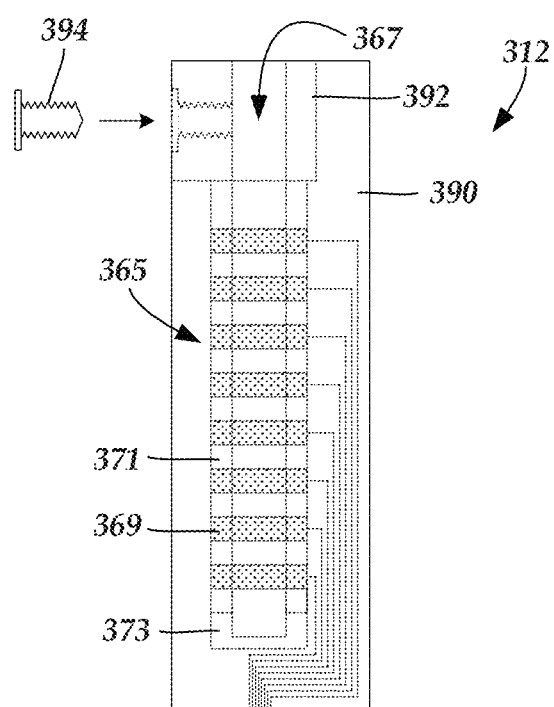
FIG. 3 is a schematic side view of one embodiment of a lead extension suitable for coupling with the electrical stimulation lead of FIG. 2, according to the invention.
Figure 3:
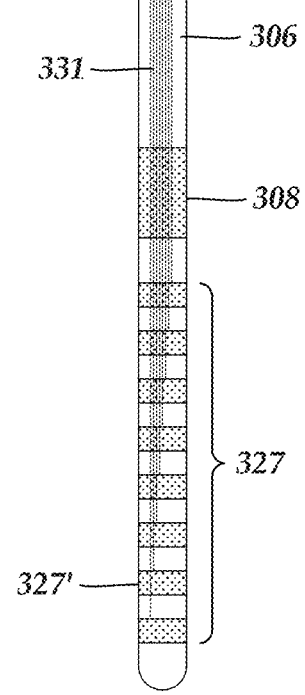

FIG. 3 shows, in schematic side view, one embodiment of a lead extension 312 suitable for implanting into a patient and coupling a lead, such as the lead 212, to a control module. The lead extension 312 includes a lead-extension body 306 having a distal portion and a proximal portion. A lead-extension connector 390 is disposed along the distal portion of the lead-extension body 306 and an array of lead-extension terminals 327, such as lead-extension terminal 327', are disposed along the proximal portion of the lead-extension body 306.

The lead-extension connector 390 contains a lead-extension connector stack 365 that defines a connector lumen 367 configured to receive the proximal portion of an elongated member (e.g., lead 212). The lead-extension connector stack 365 includes lead-extension connector contacts, such as lead-extension connector contact 369, arranged along the connector lumen 367 and configured to electrically couple with terminals of the elongated member (e.g., lead 212) when the proximal portion of the elongated member is received by the lead-extension connector 390. The connector contacts can be electrically isolated from one another by electrically-nonconductive spacers, such as spacer 371. The connector stack may also include an end stop 373 to promote alignment of the elongated-member terminals with the lead-extension connector contacts.

The lead-extension connector 390 further includes a retention assembly for facilitating retention of the proximal portion of the elongated member (e.g., lead 212) when the proximal portion of the elongated member is received by the lead-extension connector 390. In the illustrated embodiment, the retention assembly includes a lead-extension retention block 392. The lead-extension retention block 392 is positioned to align with the auxiliary terminal (208 in FIG. 2) of the elongated member when the elongated member is received by the lead-extension connector 390. In the illustrated embodiment, the retention assembly further includes a retaining member (e.g., a set screw, a pin, or the like) 394 for pressing the auxiliary terminal of the inserted elongated member against the retention block to retain inserted elongated member within the lead-extension connector 390.

Lead-extension conductors, such as lead-extension conductor 331, extend along a longitudinal length of the lead extension and electrically couple the lead-extension connector contacts to the array of lead-extension terminals 327. The lead-extension conductors can extend along the longitudinal length of the lead-extension body within one or more lumens defined in the lead extension. In other instances, the lead-extension conductors may extend along the lead extension within the lead-extension body itself. The lead extension 312 includes an auxiliary terminal 308 disposed along the proximal portion of the lead-extension body to facilitate coupling of the proximal portion of the lead extension to a connector, such as a control-module connector, another lead-extension connector, or the like.

Figure 4:
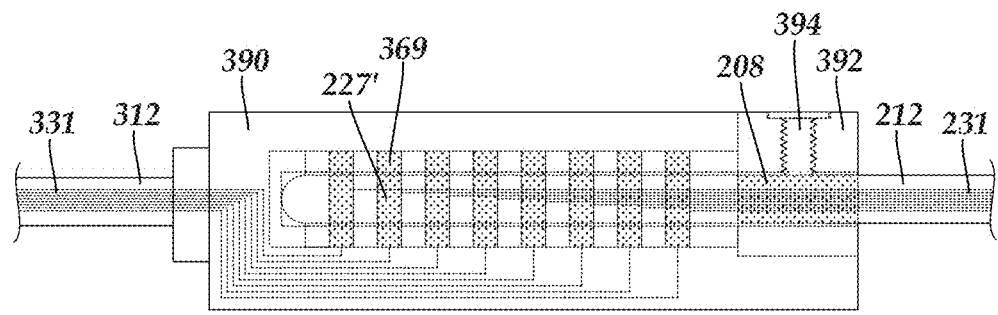
FIG. 4 is a schematic side view of one embodiment of the lead of FIG. 2 coupled to the lead extension of FIG. 3, according to the invention.

FIG. 4 shows, in schematic side view, one embodiment of the lead 212 received by the lead-extension connector 390. In the illustrated embodiment, the lead terminals 227, such as lead terminal 227', are aligned with the lead-extension connector contacts, such as lead-extension connector contact 369. Accordingly, the lead conductors 231 are electrically coupled with the lead-extension conductors 331. Additionally, in the illustrated embodiment the lead auxiliary terminal 208 is aligned with the lead-extension retention block 392 and the retaining member 394 is pressing the lead auxiliary terminal 208 against the lead-extension retention block to retain the lead 212 within the lead-extension connector 390.

Figure 5:
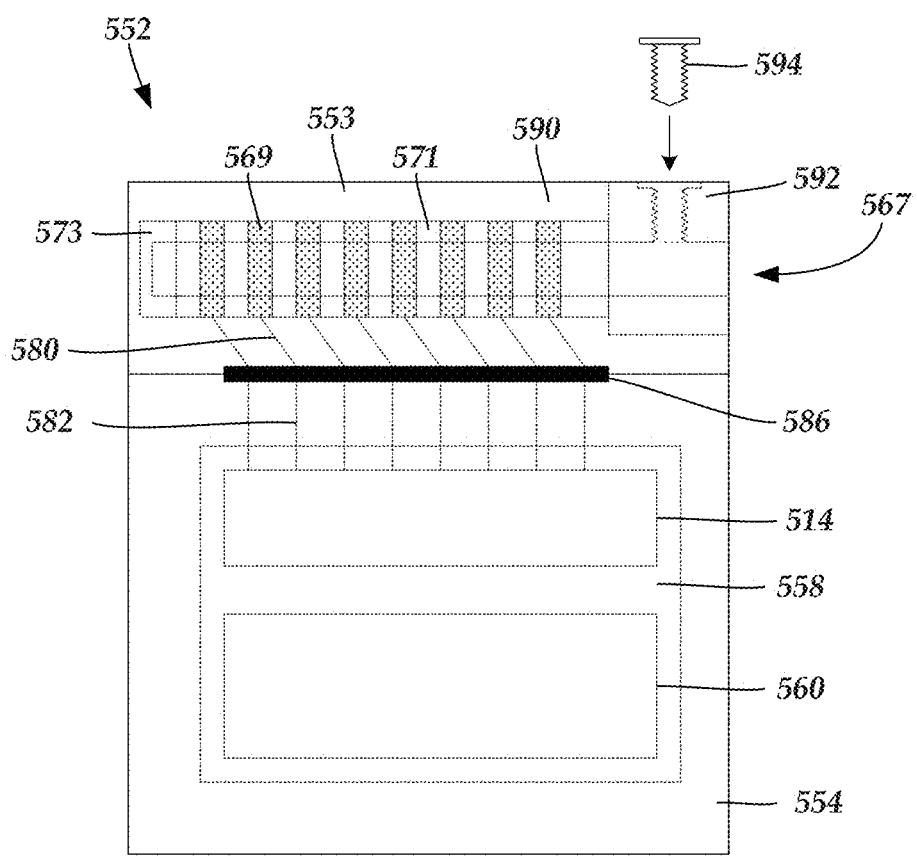
FIG. 5 is a schematic side view of one embodiment of a control module suitable for receiving either the lead of FIG. 2 or the lead extension of FIG. 3, according to the invention.

FIG. 5 shows, in schematic cross-sectional side view, a control module 552 suitable for coupling with an elongated member (e.g., the lead 212, the lead extension 312, or other intermediary device). The control module 552 includes a header 553 disposed along an outer surface of a sealed housing 554 that contains an electronic subassembly 558 with a pulse generator 514 and, optionally, a power supply 560.

A connector assembly 590 is disposed in the header 553. The connector assembly 590 is configured to receive an elongated device (e.g., the lead 212, the lead extension 312, or other intermediary device). The connector assembly 590 defines a connector lumen 567 configured to receive the proximal portion of the elongated member. An array of connector contacts, such as connector contact 569, is arranged along the connector lumen 567 and configured to electrically couple with terminals of the elongated member when the proximal portion of the elongated member is received by the connector 590. The connector contacts can be electrically isolated from one another by electrically-nonconductive spacers, such as spacer 571. The connector stack may also include an end stop 573 to promote alignment of the elongated-member terminals with the connector contacts.

Feedthrough interconnects, such as feedthrough interconnect 582, are electrically coupled to the electrical subassembly 558 and extend within the sealed housing 554 to a feedthrough interface 586 disposed along an interface between the header 553 and the sealed housing 554. The connector contacts are electrically coupled to interconnect conductors, such as interconnect wire 580, that extend along the header 553 and electrically couple the connector contacts to the feedthrough interconnects at the feedthrough interface 586. In some embodiments, the header 553 is positioned over the feedthrough interface 586.

The connector assembly 590, optionally, includes a retention assembly for facilitating retention of the proximal portion of the elongated member when the proximal portion of the elongated member is received by the control module 552. In the illustrated embodiment, the retention assembly includes a retention block 592. The retention block 592 is positioned to align with a retention sleeve (see e.g., 608 in FIG. 6) of the elongated member when the elongated member is received by the connector assembly 590. In the illustrated embodiment, the retention assembly further includes a retaining member (e.g., a set screw, a pin, or the like) 594 for pressing the retention sleeve of the inserted elongated member against the retention block to retain inserted elongated member within the connector assembly 590.

Figure 6:
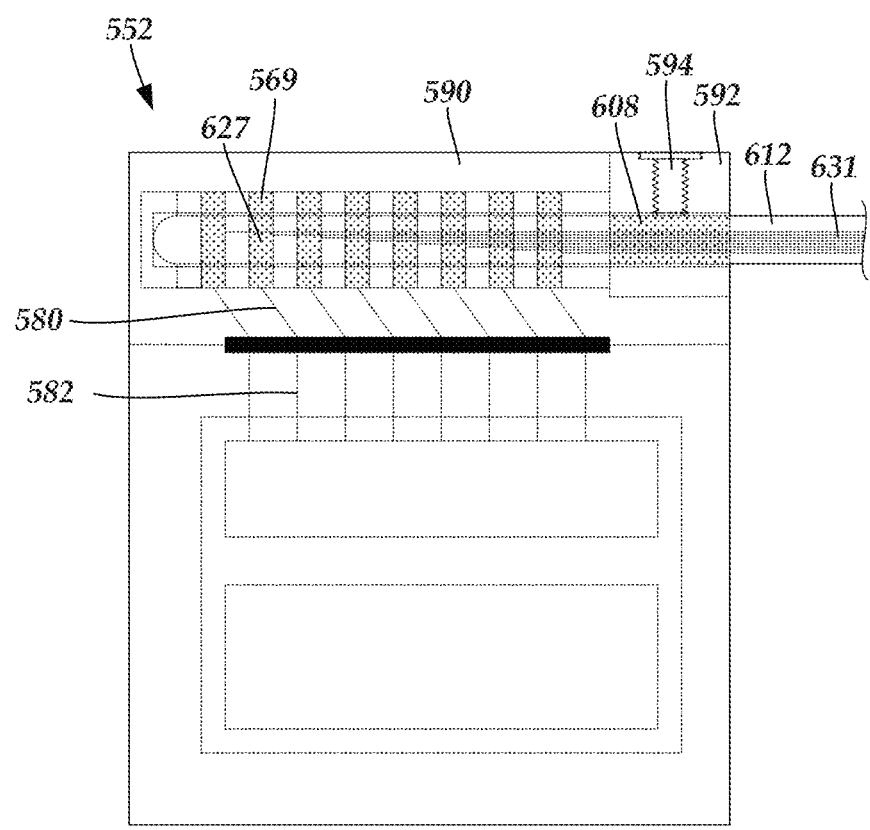
FIG. 6 is a schematic side view of one embodiment of an elongated member retained by the control module of FIG. 5, according to the invention.

FIG. 6 shows, in schematic side view, one embodiment of an elongated member 612 (e.g., the lead 212, the lead extension 312, or other intermediary device) received by the connector assembly 590 of the control module 552. In the illustrated embodiment, the elongated-member terminals, such as elongated-member terminal 627, are aligned with the connector contacts, such as connector contact 569. Accordingly, the elongated-member conductors 631 are electrically coupled with the interconnect conductors 580 and feedthrough interconnects 582. Additionally, in the illustrated embodiment a retention sleeve 608 disposed along the elongated member 612 is aligned with the retention block 592 and the retaining member 594 is pressing the retention sleeve 608 against the retention block 592 to retain the elongated member 612 within the connector assembly 590.

Connector assemblies are often disposed within headers disposed over sealed housings containing an electronic subassembly (e.g., the IPG). Conventional headers are unsealed and are typically formed using casting techniques. Interconnect conductors used to electrically couple connector contacts with the electronic subassembly are often arranged along the header in complicated wiring configurations encased in epoxy. Interconnect conductors cannot typically couple the connector contacts directly to the electronic subassembly because the header is positioned external to the sealed housing. Instead, the interconnect conductors typically couple the connector contacts to feedthrough interconnects that extend from the electronic subassembly to a feedthrough interface positioned along an outer surface of the sealed housing.

Connector assemblies formed along unsealed, or non-hermetic, portions of control modules may include locations prone to undesired current leakage. Many such potential locations occur along portions of the interconnect conductors. For example, current leakage can occur along portions of interconnect conductors where the interconnect conductors couple with feedthrough interconnects at the feedthrough interface; between two or more non-insulated interconnect conductors; at the interface between the interconnect conductors and the connector contacts; and along portions of interconnect conductors breaching outer surfaces of the casted header.

It may be advantageous to reduce, or even eliminate, current leakage. Reducing, or even eliminating, current leakage may improve therapy, increase the implantable lifespan of the control module, and improve manufacturing (e.g., removing the step of forming, such as casting, a header). Additionally, it may be advantageous to form the feedthrough as an integral part of the connector wiring to generate cost savings. Such a design may further increase the implantable lifespan of the control module, and further improve manufacturing (e.g., reducing, or even eliminating the use of epoxy, eliminating the need for an electrical connection between interconnect conductors and feedthrough interconnects).

Figure 7:
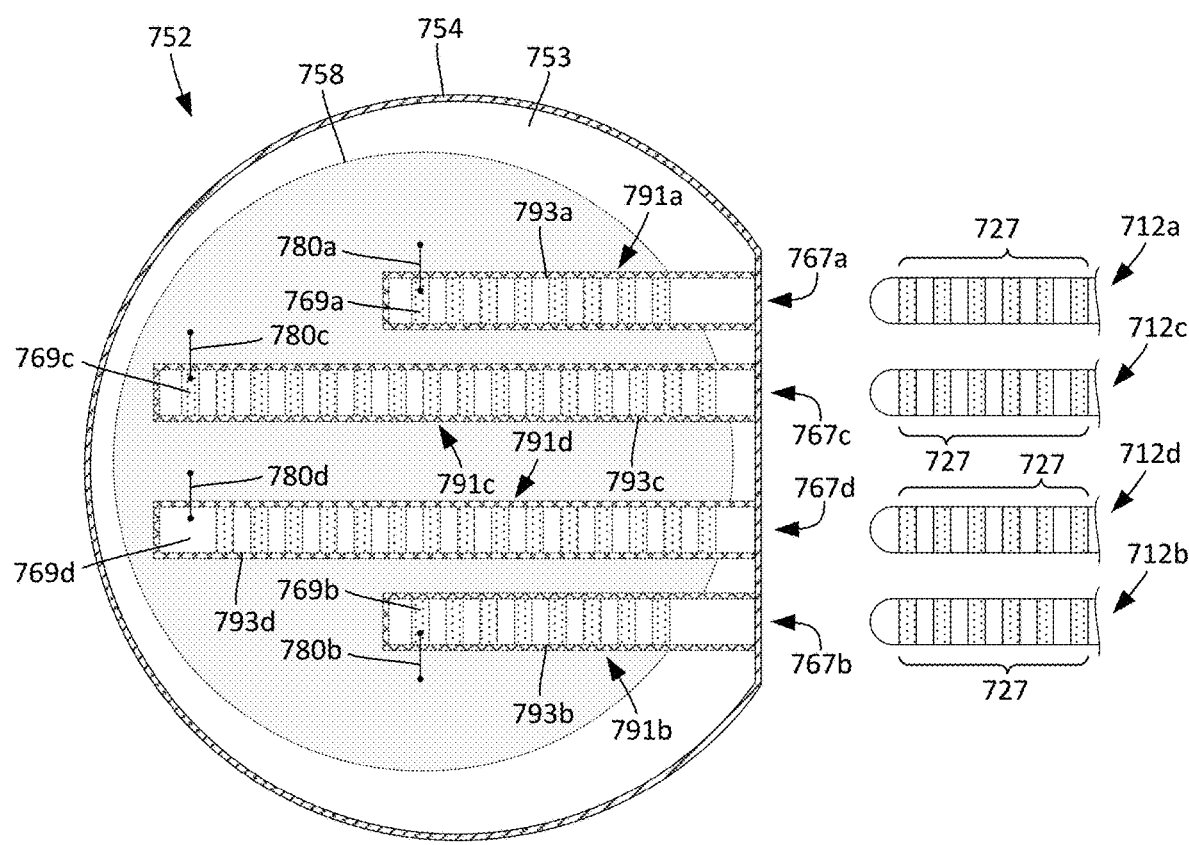
FIG. 7 is a schematic top view of one embodiment of a control module with connector shells extending within a housing of the control module and forming a sealed cavity therewith, and portions of elongated members suitable for insertion into the connector shells, according to the invention.

Turning to FIG. 7, as herein described an enhanced connector assembly reduces potential exposure to current leakage from conventional connector assemblies. In at least some embodiments, the connector assembly includes a connector shell that is hermetically, or near-hermetically, sealed. Although the connector shell can be disposed in a header (e.g., header 553 of FIG. 5), it does not need to be. Thus, in at least some embodiments, control modules within which the connector shells are disposed do not include headers.

The interconnect conductors extend from the one or more connector shells within the sealed housing of the control module. Accordingly, the interconnect conductors do not need to be formed from noble metals or be encased in epoxy. In at least some embodiments, utilizing the connector shells reduces the amount of, or even eliminates, epoxy used in the connector. In at least some embodiments, the connector shell enables interconnect conductors to directly couple connector contacts to the electronic subassembly of the control module, thereby eliminating the need for feedthrough interconnects.

FIG. 7 illustrates, in schematic top view, a control module 752 suitable for implanting into a patient and coupling to an electrical stimulation lead. The control module 752 includes an electronic subassembly 758 disposed in a sealed cavity 753 of a housing 754. The control module further includes one or more connector assemblies for receiving one or more elongated members (e.g., leads or lead extensions) and electrically coupling terminals of a received elongated member to the electronic subassembly 758. In the illustrated embodiment, the control module 752 is shown with four connector assemblies 791a-d.

The connector assemblies each include at least one connector contact arranged along a connector lumen defined in a connector shell. The connector shell(s) extend(s) into the housing 754. The connector shell(s), along with the housing 754, collectively form the sealed cavity 753.

The connector contacts are suitable for electrically coupling with terminals of elongated members when the elongated members are received by the connector lumens. In the illustrated embodiment, connector assembly 791a includes connector contacts, such as connector contact 769a, arranged along connector lumen 767a defined in a connector shell 793a; connector assembly 791b includes connector contacts, such as connector contact 769b, arranged along connector lumen 767b defined in a connector shell 793b; connector assembly 791c includes connector contacts, such as connector contact 769c, arranged along connector lumen 767c defined in a connector shell 793c; and connector assembly 791d includes connector contacts, such as connector contact 769d, arranged along connector lumen 767d defined in a connector shell 793d.

The connector assemblies can be configured for receiving elongated members with different numbers of terminals including, for example, 1, 2, 4, 8, 12, 16, 24, or more terminals. Additionally, different numbers of connector assemblies can be disposed in the control module including, for example, one, two, three, four, six, eight, or more connector assemblies.

In the illustrated embodiment, the connector assemblies 791a, 791b each include eight connector contacts. Accordingly, the connector assemblies 791a, 791b are each configured to receive elongated members 712a, 712b, respectively, each having eight terminals 727. The connector assemblies 791c, 791d each include sixteen connector contacts. Accordingly, the connector assemblies 791c, 791d are each configured to receive elongated members 712c, 712d, respectively, each having sixteen terminals 727.

Interconnect conductors electrically couple the connector contacts to the electronic subassembly 758. In the illustrated embodiment, interconnect wire 780a electrically couples connector contact 769a to the electronic subassembly 758; interconnect wire 780b electrically couples connector contact 769b to the electronic subassembly 758; interconnect wire 780c electrically couples connector contact 769c to the electronic subassembly 758; and interconnect wire 780d electrically couples connector contact 769d to the electronic subassembly 758.

In FIG. 7, for each of the connector assemblies 791a-d a connection between a single connector contact and the electronic subassembly is shown, for clarity of illustration. In at least some embodiments, each connector contact of each connector assembly is coupled to the electronic subassembly. In at least some embodiments, each connector contact is coupled to the electronic subassembly via a different interconnect wire that extends from the connector shell to the electronic subassembly within the sealed cavity 753.

Figure 8:
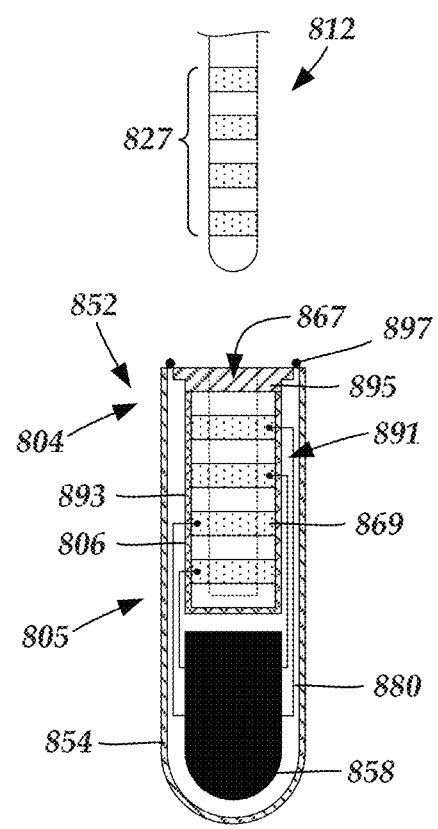
FIG. 8 is a schematic longitudinal cross-sectional view of another embodiment of a control module with a connector shell extending within a housing of the control module and forming a sealed cavity therewith, and a portion of an elongated member suitable for insertion into the connector shell, according to the invention.

The control module can be formed in any suitable arrangement to accommodate the components of the control module including, for example, the connector shell(s), the electronic subassembly, and the electrical connections extending therebetween. FIG. 8 illustrates, in schematic longitudinal cross-sectional view, another embodiment of a control module 852 suitable for implanting into a patient and coupling to an electrical stimulation lead. The control module 852 includes an electronic subassembly 858 disposed in a sealed housing 854.

The control module further includes a connector assembly for receiving an elongated member (e.g., a lead or lead extension) and electrically coupling terminals of the received elongated member to the electronic subassembly 858. In the illustrated embodiment, the control module 852 is shown with a single connector assembly 891. The connector assembly 891 includes connector contacts, such as connector contact 869, arranged along connector lumen 867 defined in connector shell 893. In the illustrated embodiment, the connector assembly 891 includes four connector contacts and is configured to receive an elongated member 812 with four terminals 827.

The connector shell 893 has an elongated shape with a first end 804, an opposing second end 805, and a sidewall 806. The first end 804 of the connector shell is open to receive the elongated member. The illustrated embodiment shows an optional flange 895 disposed along the open first end 804 of the of the connector shell 893. The flange 895 may be useful for facilitating insertion of the elongated member into the connector shell. The flange 895 can be attached to the connector shell using any suitable technique (e.g., brazing, welding, co-firing, or the like). A hermetic weld 897 is formed around a perimeter of the first end 804 of the connector shell 893 (or a perimeter of the flange, if applicable) to seal the connector shell 893 with the housing 854.

In at least some embodiments, the connector assembly includes a strain relief disposed in proximity to the open first end 804 of the connector shell. In at least some embodiments, the connector assembly includes a retention assembly (see e.g., retention block 592 and retaining member 594 of FIG. 5) for facilitating retention of the elongated member when the elongated member is received by the connector assembly. In at least some embodiments, the connector assembly is closed at the second end 805. In at least some embodiments, the connector assembly includes an end stop (see e.g., end stop 573 of FIG. 5) disposed along the second end 805 of the connector shell 893.

The arrangements shown in FIGS. 7 and 8 are exemplary. In other embodiments, control modules are formed to receive a single elongated member, or multiple elongated members each having the same number of terminals. As shown in FIG. 7, in embodiments where multiple connector shells are utilized, and where the connector shells include different numbers of connector contacts, longer connector lumens may be needed to accommodate the connector shells with the comparatively higher numbers of connector contacts. It may be advantageous to arrange comparatively longer-lumened connector shells medial to shorter-lumened connector shells to increase efficiency of size when the housing 754 has rounded shape, as is shown in FIG. 7.

In FIG. 7, the connector shells are oriented relative to the electronic subassembly such that the electronic subassembly is in proximity to the sidewalls of the connector shells. In FIG. 8, the connector shell is oriented relative to the electronic subassembly such that the electronic subassembly is in proximity to the second end 805 of the connector shell. The orientation of the connector shell relative to the electronic subassembly can be modified to enable the shape of the control module to accommodate the positioning of implantation, or ease of use, or other purposes or reasons.

Turning to FIGS. 9A-9D, in some embodiments, the connector shell is formed from an electrically nonconductive material including, for example, glass, ceramic(s), or combinations thereof. The connector shell is open at one end and closed at an opposing end. In at least some embodiments, the connector shell is formed as a tube.

In at least some embodiments, the connector shell defines one or more interconnect apertures along the sidewall (longitudinal length) of the connector shell. The interconnect apertures facilitate electrical coupling of the connector contacts to the electronic subassembly by interconnect conductors.

The interconnect apertures can be hermetically sealed using either electrically conductive material (e.g., solder, cermet, or the like), or electrically nonconductive material (e.g., glass or ceramic). In at least some embodiments, the interconnect apertures are sealed using vias electrically coupled to the connector contacts. In at least some embodiments, the vias are formed after the interconnect conductors are extended through the interconnector apertures and electrically coupled to connector contacts. In other embodiments, the vias are formed before the interconnect conductors are coupled to the connector contacts, and the interconnect conductors electrically couple to the connector contacts by electrically coupling to the vias. In at least some embodiments, the vias are brazed to walls of the interconnect apertures. In other embodiments, the vias are welded to walls of the interconnect apertures.

Figure 9A:
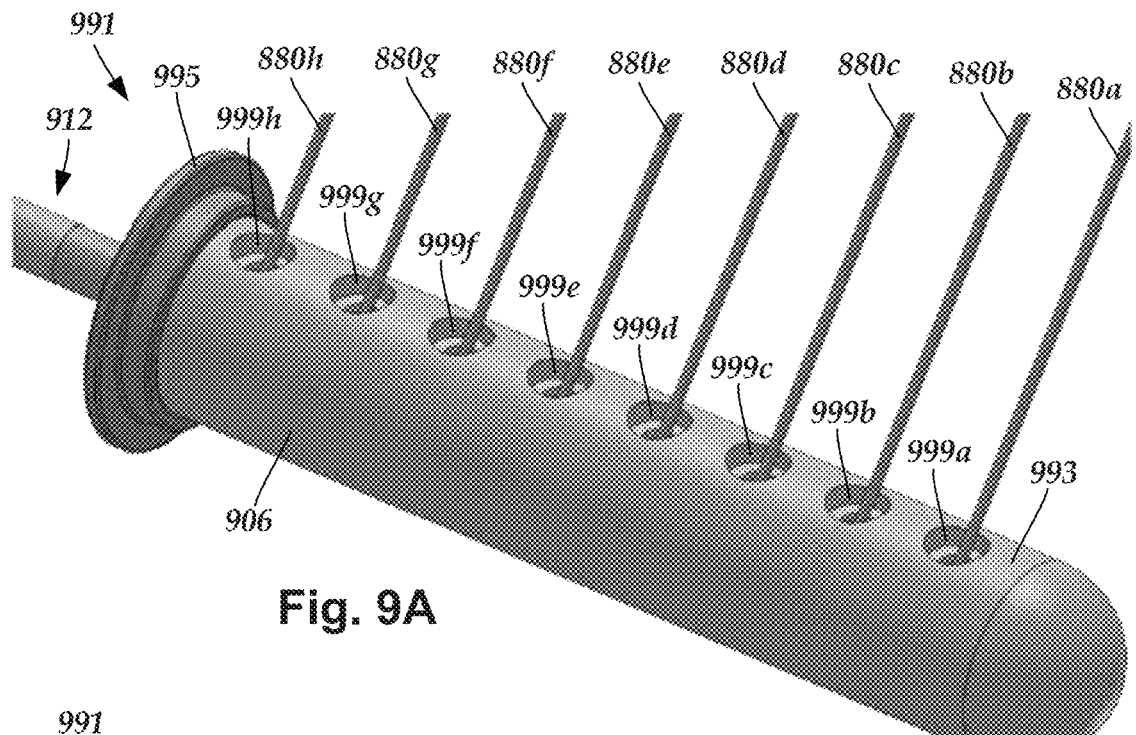
FIG. 9A is a schematic perspective view of one embodiment of an elongated member disposed in a connector shell with interconnect conductors electrically coupled to connector contacts within the connector shell via interconnect apertures defined along a sidewall of a connector shell, according to the invention.
Figure 9B:
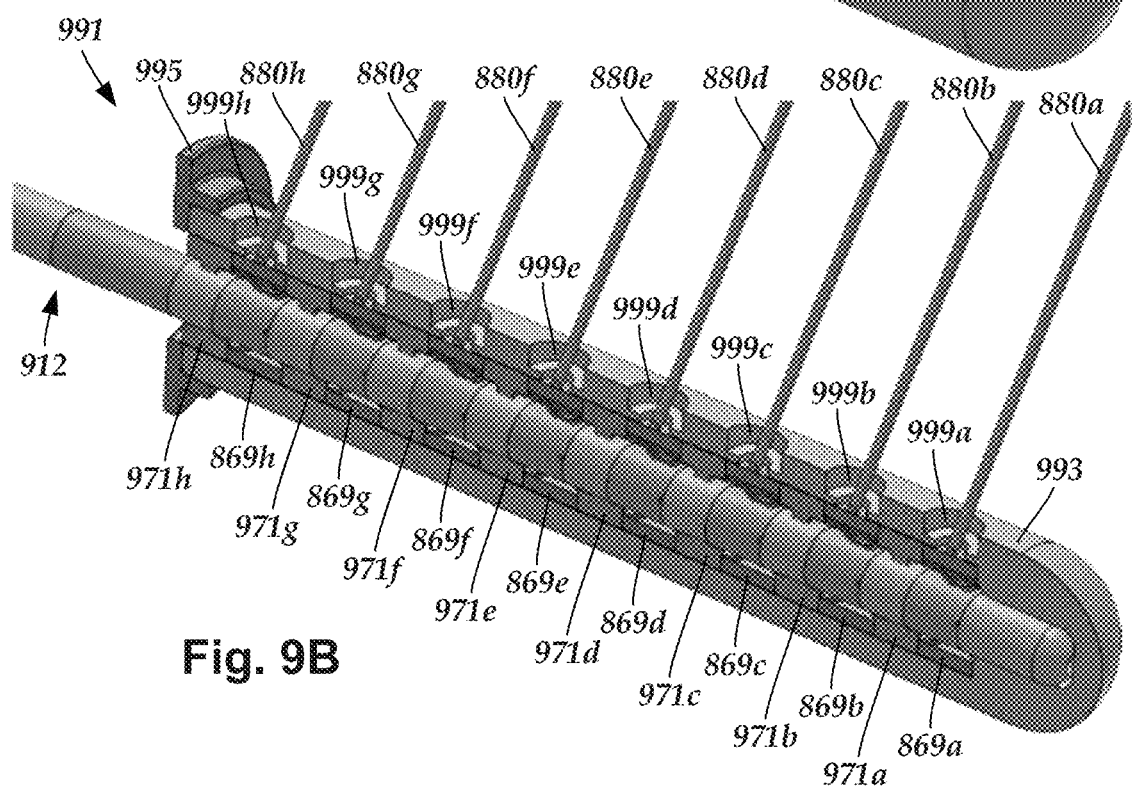
FIG. 9B is a schematic perspective view of one embodiment of the elongated member of FIG. 9A disposed in a longitudinal cross-sectional view of the connector assembly of FIG. 9A, according to the invention.
Figure 9C:
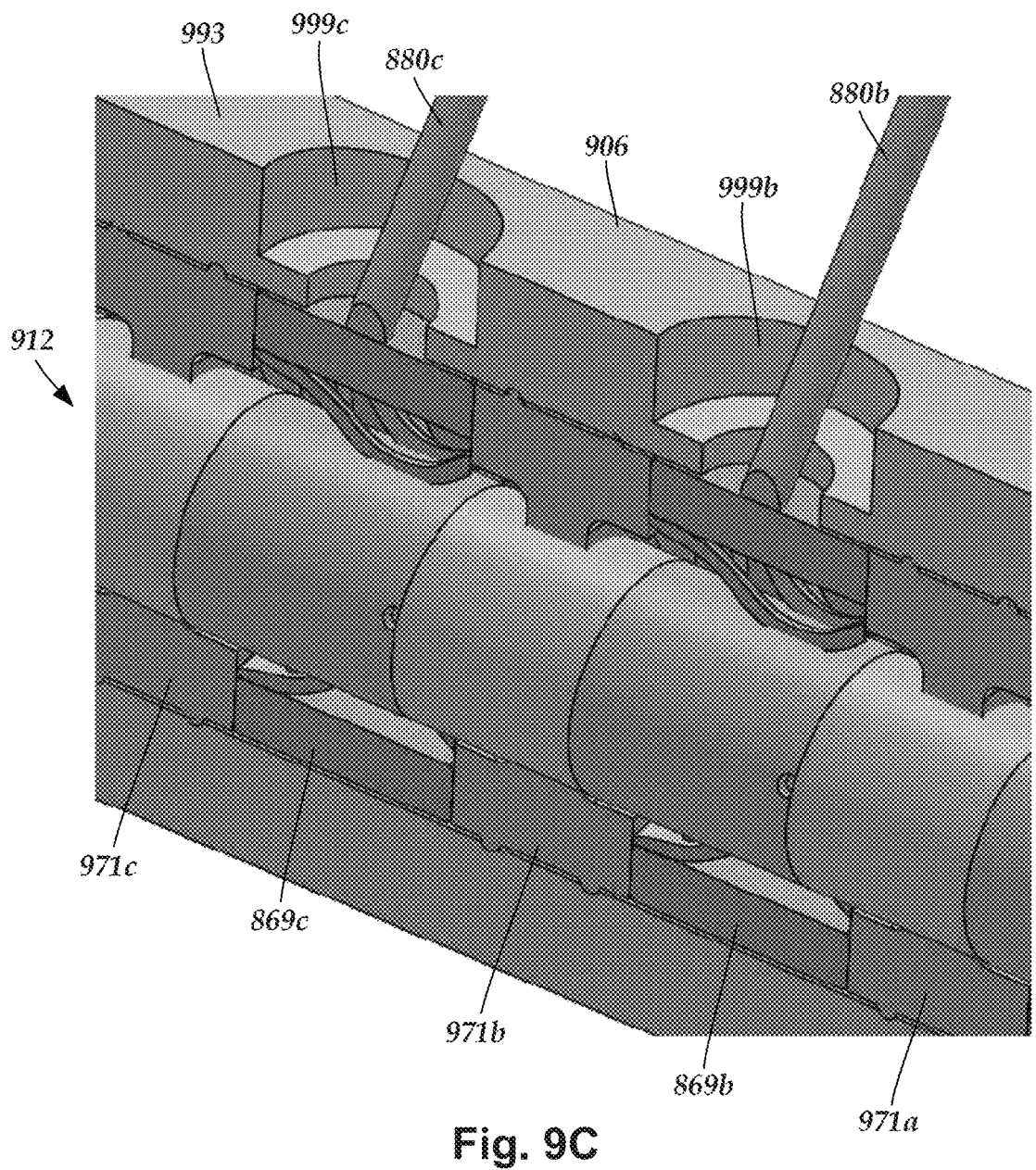
FIG. 9C is a close-up view of a portion of the schematic perspective view of one embodiment of the elongated member of FIG. 9B disposed in the longitudinal cross-sectional view of the connector assembly of FIG. 9B, according to the invention.
Figure 9D:
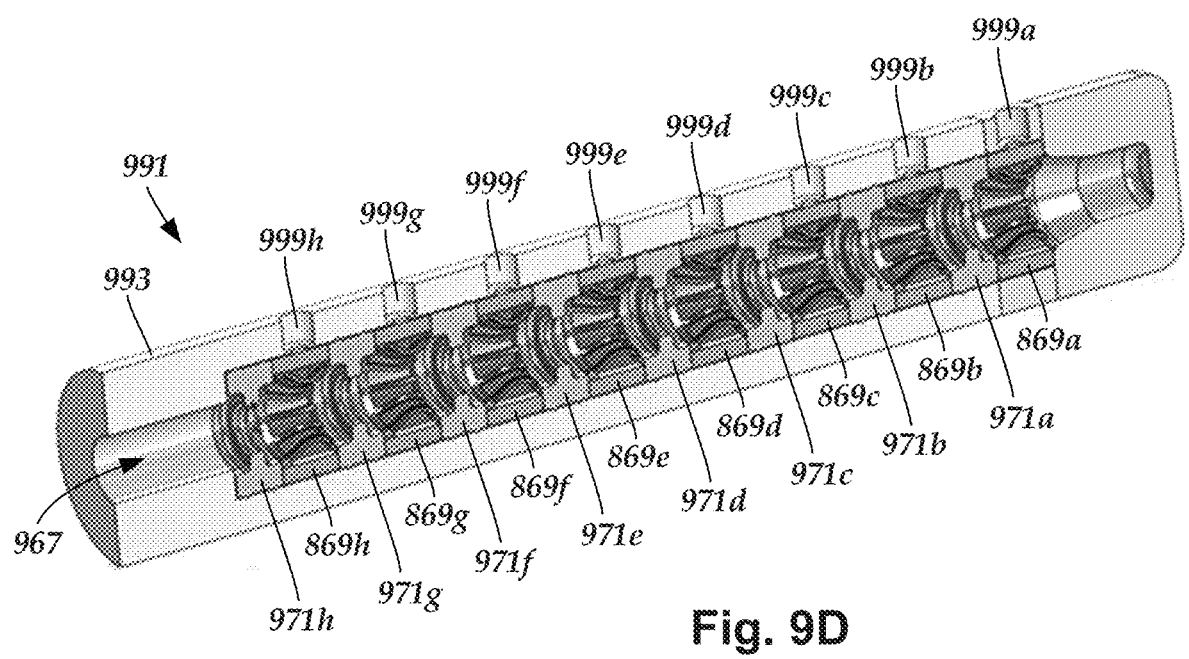
FIG. 9D is a schematic perspective, longitudinal cross-sectional view of one embodiment of the connector assembly of FIGS. 9A-9C, according to the invention.

FIG. 9A shows, in schematic perspective view, an elongated member 912 (e.g., a lead or a lead extension) disposed in a connector assembly 991. FIG. 9B shows the connector assembly 991 in longitudinal cross-sectional view. FIG. 9C shows a portion of the elongated member 912 disposed in a portion of the connector assembly 991 in close-up view. FIG. 9D shows the connector assembly 991 in perspective, longitudinal cross-sectional view without the elongated member 912 disposed in the connector assembly 991.

The connector assembly 991 includes connector contacts 869a-h disposed in a connector lumen 967 of a connector shell 993. The connector contacts 869a-h are physically and electrically isolated from one another by electrically nonconductive spacers 971a-h. Interconnect conductors 880a-h electrically couple with the connector contacts 869a-h, respectively, via interconnect apertures 999a-h, respectively, defined along a sidewall 906 of the connector shell 993. In the illustrated embodiment, each interconnect wire extends through a different interconnect aperture. In at least some embodiments, multiple interconnect conductors extend through at least one of the interconnect apertures.

The interconnect conductors can, in some embodiments, be electrically coupled directly to the connector contacts using any suitable technique (e.g., laser welding). The interconnect apertures can be hermetically sealed before or after the interconnect conductors are electrically-coupled to the connector contacts. In at least some embodiments, the interconnect apertures are sealed using a hermetic sealing material including, for example, metal (e.g., solder, cermet, or the like), glass, or ceramic. In embodiments with electrically conductive sealing material (e.g., vias), the interconnector conductors can, optionally, be coupled to the connector contacts indirectly by electrically coupling to the vias. In at least some embodiments, one or more of the connector contacts, interconnect conductors, and interconnect apertures surfaces are coated with one or more materials in preparation for accepting the hermetic sealing material. In at least some embodiments, one or more of the connector contacts, interconnect conductors, and interconnect apertures surfaces are preheated prior to application of the hermetic sealing material.

The connector contacts can be formed from any electrically-conductive material suitable for implantation. The connector contacts can be formed in any suitable configuration to make electrical contact with terminals of a received elongated member. In the illustrated embodiments, the connector contacts are formed as leaf springs.

Turning to FIGS. 10A-10D, in some embodiments the connector shell is formed from sections of electrically conductive material interconnected with sections of electrically nonconductive material fixedly attached together. In some embodiments, the interconnected sections of material are stacked along a longitudinal length of the connector shell. In some embodiments, the interconnected sections of material are arranged in an alternating conductive-nonconductive configuration. In some embodiments, the interconnected sections of material are formed as alternating rings of material.

FIG. 10A illustrates, in schematic perspective, explosive view, a stack of ring-shaped sections of electrically conductive material 1014a-d alternated with ring-shaped sections of electrically nonconductive material 1016a-e. FIG. 10B shows the alternating ring-shaped sections 1014a-d and 1016a-e interconnected to form a connector shell 1093 having a first end 1004, an opposing second end 1005, and a longitudinal length (indicated by two-headed arrow 1006). FIG. 10C shows the connector shell 1093 in longitudinal cross-sectional view.

As shown in FIG. 10A, the alternating ring-shaped sections 1014a-d and 1016a-e each define a central aperture, such as central aperture 1020. As shown in FIGS. 10B-10C, when the alternating ring-shaped sections 1014a-d and 1016a-e are stacked and interconnected, the central apertures 1020 align to collectively form a connector lumen 1067 that is open at the first end 1004 of the connector shell 1004. The illustrated embodiment includes an optional end piece 1073 disposed along the second end 1005 of the connector shell 1093. The optional end piece 1073 functions to close the second end 1005 of the connector shell 1004. In at least some embodiments, the end piece 1073 is formed from electrically nonconductive material. An optional flange 1095 can be coupled to the first end 1004 of the connector shell 1093 to facilitate insertion of an elongated member into the connector lumen 1067.

The interconnected ring-shaped sections 1014a-d and 1016a-f can be interconnected using any suitable technique including, for example, brazing, 3D printing, co-firing (low- or high-temperature). Similarly, the optional flange 1095 can be coupled to the connector shell 1093 using any suitable technique including, for example, brazing, 3D printing, co-firing (low- or high-temperature). In at least some embodiments, the ring-shaped sections (and the end piece and the flange, if applicable) are interconnected to form a hermetic seal along the sidewall (longitudinal length) and the second end of the connector shell.

In at least some embodiments, the ring-shaped sections are arranged such that each of the electrically conductive ring-shaped sections 1014a-d is separated from each of the remaining electrically conductive ring-shaped sections 1014a-d by at least one electrically nonconductive ring-shaped section 1016a-e in either direction along the longitudinal length 1006 of the connector shell 1093.

Figure 11A:
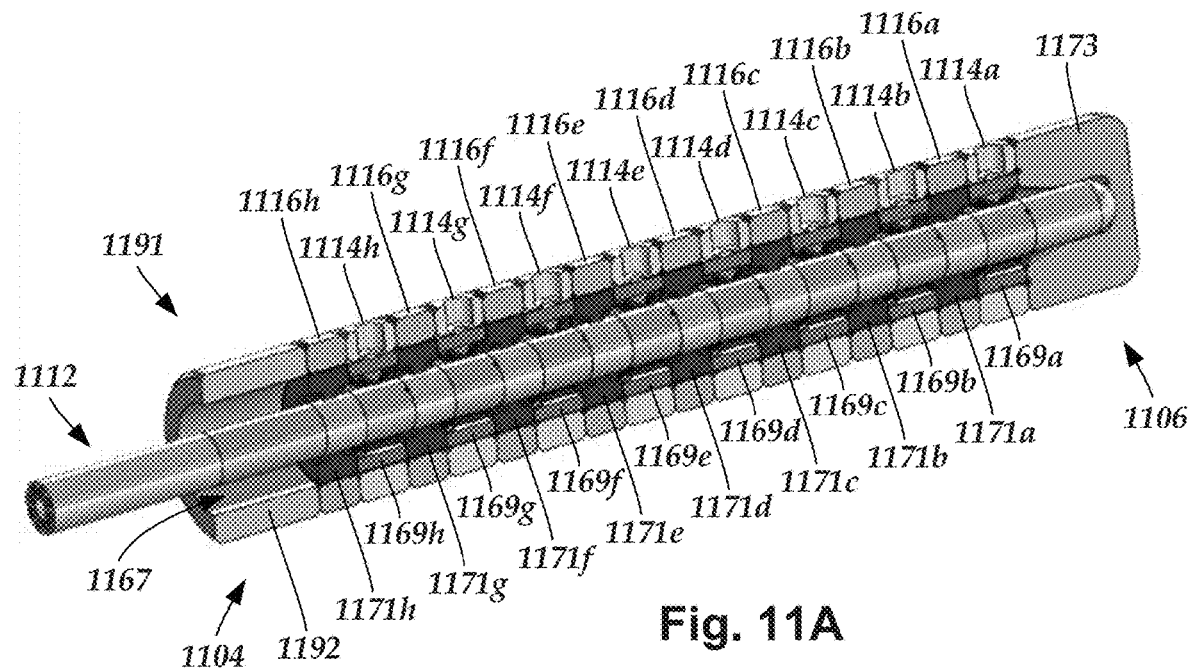
FIGS. 11A-11B are schematic perspective views of one embodiment of a portion of an elongated member disposed in a longitudinal cross-sectional view of a connector shell formed from alternating rings of electrically conductive material and electrically nonconductive material, according to the invention.
Figure 11B:
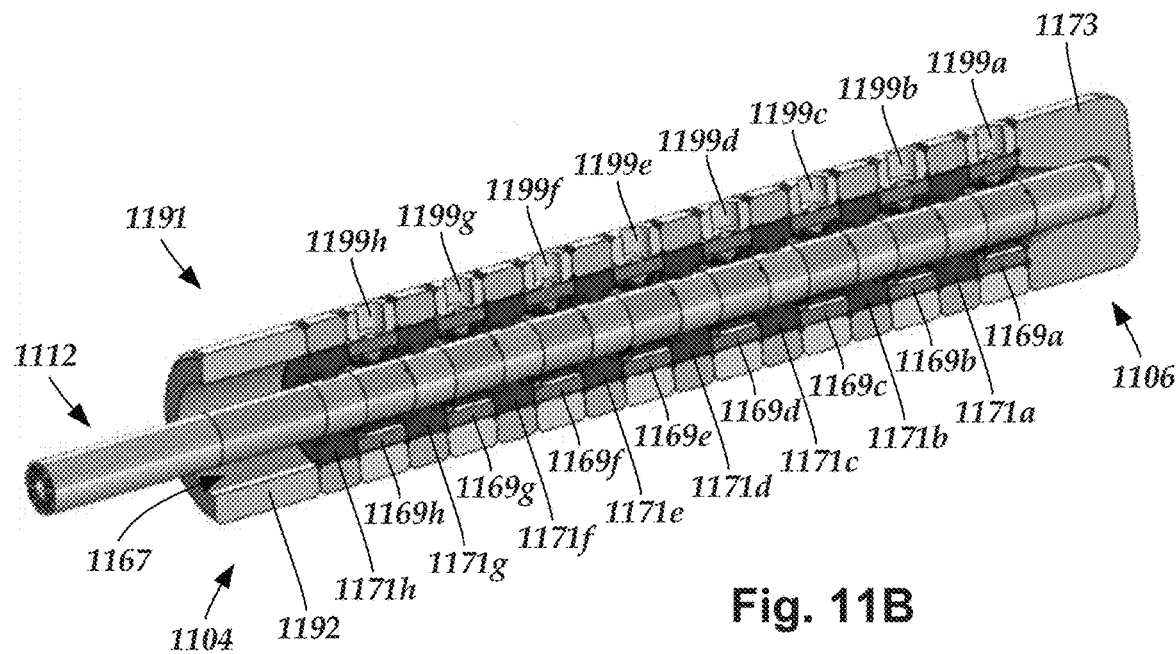

In at least some embodiments, the alternating ring-shaped sections are aligned along the longitudinal length of the connector shell with corresponding connector contacts and spacers within the connector shell. FIGS. 11A-11B show, in perspective view, a portion of an elongated member 1112 disposed in a connector assembly 1171 (shown in longitudinal cross-section). The connector assembly 1191 includes a connector shell 1193 having a first end 1104 and an opposing second end 1105, and is formed from ring-shaped sections of electrically conductive material 1114a-h arranged in an alternating configuration with ring-shaped sections of electrically nonconductive material 1116a-h. Connector contacts 1169a-h are disposed in a connector lumen 1167 of the connector shell 1193. The connector contacts 1169a-h are physically and electrically isolated from one another within the connector lumen 1167 by spacers 1171a-h.

The alternating rings can be aligned along the longitudinal length of the connector shell 1193 with corresponding connector contacts and spacers. In the illustrated embodiment, the electrically conductive rings 1114a-h are aligned along the longitudinal length of the connector shell 1193 with the connector contacts 1169a-h, respectively. In at least some embodiments, the electrically conductive rings 1114a-h are electrically coupled to the connector contacts 1169a-h, respectively, to which they are longitudinally aligned. In at least some embodiments, the electrically nonconductive rings 1116a-h are aligned along the longitudinal length of the connector shell 1193 with the spacers 1171a-h.

In at least some embodiments, one or more interconnect apertures are defined along sidewalls of the connector shell 1193 to facilitate electrical coupling of interconnect conductors to the connector contacts. In the illustrated embodiment, interconnect apertures 1199a-h are defined along sidewalls of the electrically conductive rings 1114a-h. The interconnect apertures 1199a-h are suitable for enabling interconnect conductors (not shown in FIGS. 11A-11B) to electrically couple with the connector contacts 1169a-h, as described above with reference to FIGS. 9A-9D.

In other embodiments, interconnect conductors are electrically coupleable to connector contacts 1169a-h by coupling the interconnect conductors to a cavity-facing surface (see e.g., FIG. 7) of the electrically conductive rings aligned with, and electrically coupled to, the connector contacts. For example, in at least some embodiments an interconnect conductor is electrically coupleable to connector contact 1169a by electrically coupling the interconnect wire to a cavity-facing surface of the electrically conductive ring 1114a which, in turn, is electrically coupled to the connector contact 1169a. In such an embodiment, the interconnect conductor extends entirely within the sealed cavity of the control module.

FIGS. 11A-11B show a portion of an optional retention block 1192 formed along the first end 1104 of the connector shell 1193. The retention block 1192 may be used to facilitate retention of the elongated member 1112 in the connector assembly 1191. In at least some embodiments, the second end 1106 of the connector shell is closed. FIGS. 11A-11B also show an optional end stop 1173 disposed along the second end 1106 of the connector shell 1193. In at least some embodiments, the ring-shaped sections and end piece are interconnected to form a hermetic seal along the sidewall (longitudinal length) and second end of the connector shell.

Figure 12:
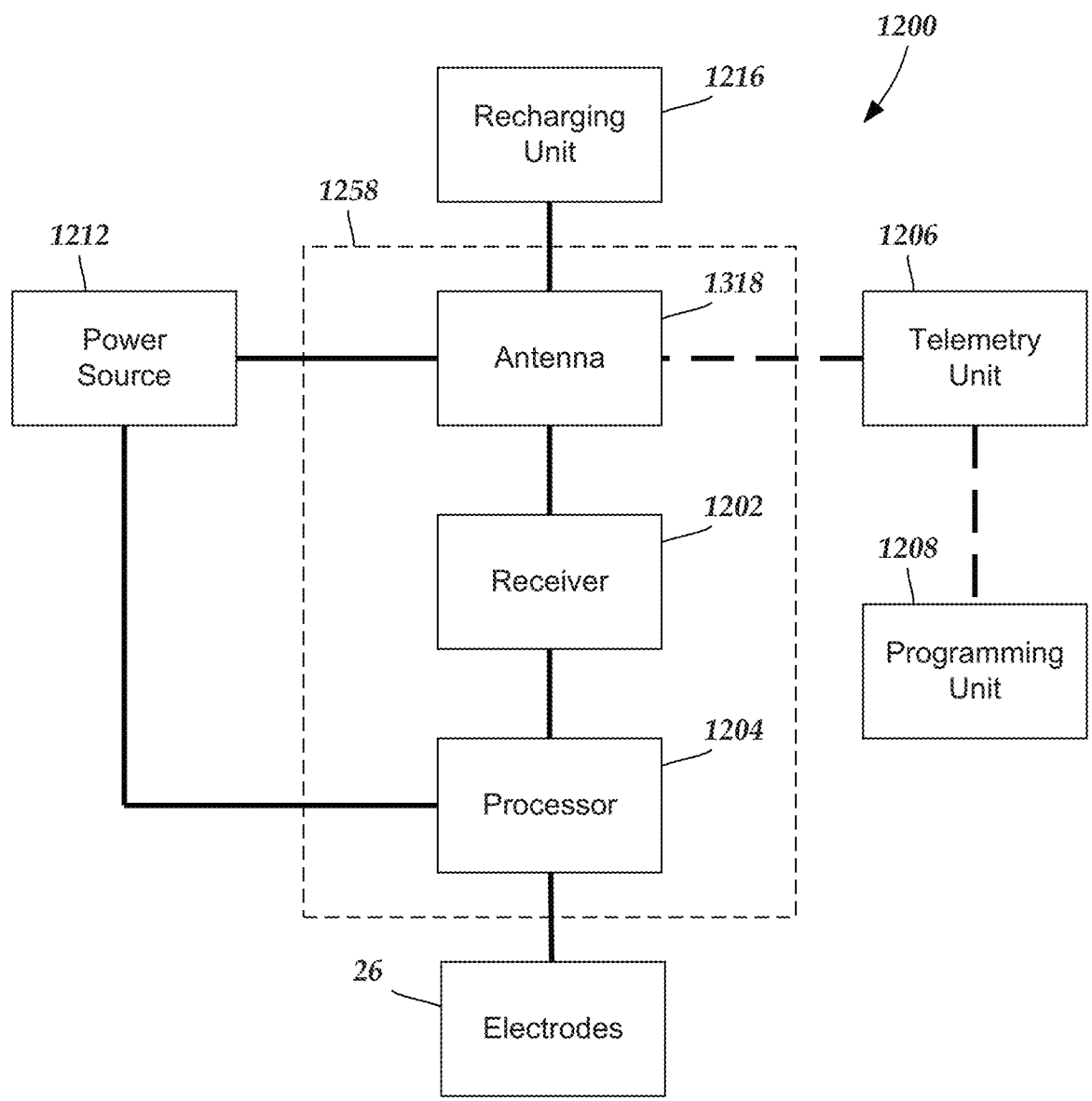
FIG. 12 is a schematic overview of one embodiment of components of a stimulation system, including an electronic subassembly disposed within a control module, according to the invention.

FIG. 12 is a schematic overview of one embodiment of components of an electrical stimulation system 1200 including an electronic subassembly 1258 disposed within a control module. The electronic subassembly 1258 may include one or more components of the IPG. It will be understood that the electrical stimulation system can include more, fewer, or different components and can have a variety of different configurations including those configurations disclosed in the stimulator references cited herein.

Some of the components (for example, a power source 1212, an antenna 1218, a receiver 1202, and a processor 1204) of the electrical stimulation system can be positioned on one or more circuit boards or similar carriers within a sealed housing of an implantable pulse generator (see e.g., 14 in FIG. 1), if desired. Any power source 1212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1218 or a secondary antenna. In at least some embodiments, the antenna 1218 (or the secondary antenna) is implemented using the auxiliary electrically-conductive conductor. The external power source can be in a device that is mounted on the skin of the user or in a unit that is provided near the user on a permanent or periodic basis.

If the power source 1212 is a rechargeable battery, the battery may be recharged using the optional antenna 1218, if desired. Power can be provided to the battery for recharging by inductively coupling the battery through the antenna to a recharging unit 1216 external to the user. Examples of such arrangements can be found in the references identified above. The electronic subassembly 1258 and, optionally, the power source 1212 can be disposed within a control module (e.g., the IPG 14 or the ETS 20 of FIG. 1).

In one embodiment, electrical stimulation signals are emitted by the electrodes (e.g., 26 in FIG. 1) to stimulate nerve fibers, muscle fibers, or other body tissues near the electrical stimulation system. The processor 1204 is generally included to control the timing and electrical characteristics of the electrical stimulation system. For example, the processor 1204 can, if desired, control one or more of the timing, frequency, strength, duration, and waveform of the pulses. In addition, the processor 1204 can select which electrodes can be used to provide stimulation, if desired. In some embodiments, the processor 1204 selects which electrode(s) are cathodes and which electrode(s) are anodes. In some embodiments, the processor 1204 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1208 that, for example, allows modification of pulse characteristics. In the illustrated embodiment, the processor 1204 is coupled to a receiver 1202 which, in turn, is coupled to the optional antenna 1218. This allows the processor 1204 to receive instructions from an external source to, for example, direct the pulse characteristics and the selection of electrodes, if desired.

In one embodiment, the antenna 1218 is capable of receiving signals (e.g., RF signals) from an external telemetry unit 1206 which is programmed by the programming unit 1208. The programming unit 1208 can be external to, or part of, the telemetry unit 1206. The telemetry unit 1206 can be a device that is worn on the skin of the user or can be carried by the user and can have a form similar to a pager, cellular phone, or remote control, if desired. As another alternative, the telemetry unit 1206 may not be worn or carried by the user but may only be available at a home station or at a clinician's office. The programming unit 1208 can be any unit that can provide information to the telemetry unit 1206 for transmission to the electrical stimulation system 1200. The programming unit 1208 can be part of the telemetry unit 1206 or can provide signals or information to the telemetry unit 1206 via a wireless or wired connection. One example of a suitable programming unit is a computer operated by the user or clinician to send signals to the telemetry unit 1206.

The signals sent to the processor 1204 via the antenna 1218 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1200 to cease operation, to start operation, to start charging the battery, or to stop charging the battery. In other embodiments, the stimulation system does not include the antenna 1218 or receiver 1202 and the processor 1204 operates as programmed.

Optionally, the electrical stimulation system 1200 may include a transmitter (not shown) coupled to the processor 1204 and the antenna 1218 for transmitting signals back to the telemetry unit 1206 or another unit capable of receiving the signals. For example, the electrical stimulation system 1200 may transmit signals indicating whether the electrical stimulation system 1200 is operating properly or not or indicating when the battery needs to be charged or the level of charge remaining in the battery. The processor 1204 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An implantable control module for an electrical stimulation system, the control module comprising:

a housing;

a connector shell extending into the housing and collectively with the housing forming a sealed cavity, the connector shell having a longitudinal length, a sidewall with a cavity-facing surface, a first end open to an environment external to the housing, and an opposing closed second end, the connector shell defining a connector lumen extending within the connector shell and open at the first end to receive a portion of a lead or lead extension, the connector shell defining a plurality of interconnect apertures through the connector shell, and a plurality of connector contacts arranged along the connector lumen within the connector shell, wherein each of the connector contacts is aligned with at least one of the interconnect apertures;

an electronic subassembly disposed in the sealed cavity; and a plurality of interconnect wires electrically coupling the electronic subassembly to the plurality of connector contacts and extending from the connector shell within the sealed cavity, wherein the interconnect wires are either a) directly attached to the connector contacts, b) directly attached to conductive material filling the interconnect apertures and directly attached to the connector contacts, or c) directly attached to the connector contacts with conductive material filling the interconnect apertures.

2. The control module of claim 1, wherein the sealed cavity is hermetically sealed.

3. The control module of claim 1, wherein the plurality of interconnect wires extends entirely within the sealed cavity.

4. The control module of claim 1, wherein the connector shell is formed from at least one of ceramic or glass.

5. The control module of claim 1, wherein the conductive material fills the interconnect apertures to form a plurality of electrically conductive vias through the sidewall of the connector shell and electrically coupled to the plurality of connector contacts.

6. The control module of claim 5, wherein each of the electrically conductive vias is aligned along the longitudinal length of the connector shell, and electrically coupled, with a different connector contact of the plurality of connector contacts.

7. The control module of claim 5, wherein the conductive material of the plurality of electrically conductive vias is brazed to the sidewall of the connector shell.

8. The control module of claim 5, wherein the conductive material of the plurality of electrically conductive vias is welded to the sidewall of the connector shell.

9. The control module of claim 5, wherein at least one interconnect wire of the plurality of interconnect wires extends through at least one electrically conductive via of the plurality of electrically conductive vias and attaches directly to one connector contact of the plurality of connector contacts.

10. The control module of claim 5, wherein at least one interconnect wire of the plurality of interconnect wires electrically couples to at least one electrically conductive via of the plurality of electrically conductive vias.

11. An electrical stimulation system comprising:
the control module of claim 1; and
an electrical stimulation lead coupleable to the control module.

12. An implantable control module for an electrical stimulation system, the control module comprising:
a housing;
a connector shell extending into the housing and collectively with the housing forming a sealed cavity, the connector shell having a longitudinal length, a sidewall with a cavity-facing surface, a first end open to an environment external to the housing, and an opposing closed second end, the connector shell defining a connector lumen extending within the connector shell and open at the first end to receive a portion of a lead or lead extension, wherein the connector shell is formed from a plurality of electrically conductive sections alternating along the longitudinal length of the connector shell with a plurality of independent electrically nonconductive sections, and wherein the electrically conductive sections and the electrically nonconductive sections are fixedly attached together, and a plurality of connector contacts arranged along the connector lumen within the connector shell;

an electronic subassembly disposed in the sealed cavity; and a plurality of interconnect conductors electrically coupling the electronic subassembly to the plurality of connector contacts and extending from the connector shell within the sealed cavity.

13. The control module of claim 12, wherein the plurality of connector contacts comprises a first connector contact, wherein the plurality of electrically conductive sections comprises a first electrically conductive section, and wherein the first connector contact is electrically coupled to the first electrically conductive section.

14. The control module of claim 13, wherein the plurality of interconnect conductors comprises a first interconnect conductor electrically coupled to the first connector contact, the first interconnect conductor attached to the first electrically conductive section along the cavity-facing surface of the connector shell.

15. The control module of claim 12, wherein the sealed cavity is hermetically sealed.

16. The control module of claim 12, wherein the connector shell is formed from at least one of ceramic or glass.

17. An electrical stimulation system comprising:
the control module of claim 12; and
an electrical stimulation lead coupleable to the control module.

18. A method for making a control module, the method comprising:
inserting a connector contact into a connector lumen extending into an open first end of a connector shell, the connector lumen configured and arranged to receive a lead or lead extension;
electrically coupling a first end of an interconnect conductor to the connector contact by forming an electrically conductive via along an interconnect aperture defined along a sidewall of the connector shell;
electrically coupling an opposing second end of the interconnect conductor to an electronic subassembly;
extending the connector shell into a housing with the first end of the connector shell open to an environment external to the housing; and
creating a sealed cavity formed collectively by the connector shell and the housing, wherein the electronic subassembly is disposed in the sealed cavity, and wherein the interconnect conductor extends from the connector shell to the electronic subassembly within the sealed cavity.

19. The method of claim 18, wherein forming an electrically conductive via along an interconnect aperture defined along a sidewall of the connector shell comprises forming the electrically conductive via around the interconnect conductor electrically coupled to the connector contact.

20. The method of claim 18, wherein electrically coupling a first end of an interconnect conductor to the connector contact comprises electrically coupling the electrically conductive via to the connector contact and electrically coupling the first end of the interconnect conductor to the electrically conductive via.

\* \* \* \* \*